United States Patent
Jakoby et al.

(10) Patent No.: US 9,417,186 B2
(45) Date of Patent: Aug. 16, 2016

(54) OPTO-ELECTRONIC SENSOR

(75) Inventors: Bernhard Jakoby, Linz (AT);
Ventsislav Lachiev, Gallneukirchen (AT); Thomas Grille, Villach (AT); Peter Irsigler, Obernberg/Inn (AT); Ursula Hedenig, Villach (AT); Sokratis Sgouridis, Annenheim (AT); Thomas Krotscheck Ostermann, Koestenberg (AT)

(73) Assignee: Infineon Technologies AG, Neubiberg (DE)

( * ) Notice: Subject to any disclaimer, the term of this patent is extended or adjusted under 35 U.S.C. 154(b) by 123 days.

(21) Appl. No.: 13/598,841

(22) Filed: Aug. 30, 2012

(65) Prior Publication Data

US 2014/0061677 A1 Mar. 6, 2014

(51) Int. Cl.
| | | |
|---|---|---|
| *H01L 33/48* | (2010.01) | |
| *G01N 21/552* | (2014.01) | |
| *G01N 21/64* | (2006.01) | |
| *G01N 21/77* | (2006.01) | |

(52) U.S. Cl.
CPC ............ *G01N 21/552* (2013.01); *G01N 21/648* (2013.01); *G01N 21/7703* (2013.01); *G01N 21/7746* (2013.01)

(58) Field of Classification Search
CPC .... H01L 31/00; G01N 21/552; G01N 21/648; G01N 21/7703; G01N 33/54373; G01N 2021/1704; G01N 21/7746; G02B 6/102; G02B 6/122; G02B 6/4214; G02B 6/12004; G02B 6/124; G02B 6/42; G02B 6/262; G02B 6/43; G02B 2006/12147; G02B 2006/12107; H01S 5/021
USPC ............................................................ 257/385
See application file for complete search history.

(56) References Cited

U.S. PATENT DOCUMENTS 6,396,984 B1 * 5/2002 Cho et al. ......................... 385/43
8,106,379 B2 1/2012 Bowers
(Continued)

OTHER PUBLICATIONS

Dipl.-Ing. Juergen Kasberger; "Theoretical and Experimental Investigations Towards a Fully Integrated Evanescent Field IR-Absorption Sensor", Johannes Kepler Universitaet Linz, Technisch-Naturwissenschaftliche Fakultaet, Sep. 2009, p. 1-131.

*Primary Examiner* — Ermias Woldegeorgis
*Assistant Examiner* — John Bodnar
(74) *Attorney, Agent, or Firm* — Eschweiler & Associates, LLC

(57) ABSTRACT

Some embodiments of the present disclosure relate to an infrared (IR) opto-electronic sensor having a silicon waveguide implemented on a single silicon integrated chip. The IR sensor has a semiconductor substrate having a silicon waveguide extends along a length between a radiation input conduit and a radiation output conduit. The radiation input conduit couples radiation into the silicon waveguide, while the radiation output conduit couples radiation out from the silicon waveguide. The silicon waveguide conveys the IR radiation from the radiation input conduit to the radiation output conduit at a single mode. As the radiation is conveyed by the silicon waveguide, an evanescent field is formed that extends outward from the silicon waveguide to interact with a sample positioned between the radiation input conduit and the radiation output conduit.

16 Claims, 9 Drawing Sheets

(56) References Cited

U.S. PATENT DOCUMENTS

| | | | |
|---|---|---|---|
| 2003/0133682 A1* | 7/2003 | Temkin | G02B 6/132 385/132 |
| 2005/0141808 A1* | 6/2005 | Cheben | G02B 6/12019 385/31 |
| 2006/0188401 A1* | 8/2006 | Robotti | B01L 3/502715 422/82.05 |
| 2007/0211985 A1* | 9/2007 | Duer | G01N 21/253 385/12 |
| 2008/0069491 A1* | 3/2008 | Kissa | G02F 1/0123 385/2 |
| 2008/0101744 A1* | 5/2008 | Keyser | G01N 21/7703 385/12 |
| 2009/0087137 A1* | 4/2009 | Doan | 385/14 |
| 2009/0103099 A1* | 4/2009 | Debackere | B82Y 20/00 356/445 |
| 2010/0164655 A1* | 7/2010 | Kawaguchi | H01P 1/042 333/254 |
| 2012/0088230 A1* | 4/2012 | Givens | G01N 21/0303 435/5 |
| 2013/0029038 A1* | 1/2013 | Bickham | G02B 6/0288 427/163.2 |

* cited by examiner

OPTO-ELECTRONIC SENSOR

BACKGROUND

Electronic sensors measure a physical quantity and convert the measured physical quantity into a signal that is provided to an electronic instrument (e.g., integrated chip processor). In recent years, the number of areas using sensors has vastly expanded. For example, sensors can be found in diverse applications such as chemical agent detection units, medical diagnostic equipment, industrial process controls, pollution monitoring, automobiles, etc.

Infrared sensors such as for instance mid-infrared (IR) sensors measure radiation emitted in the infrared (IR) portion of the electro-magnetic spectrum from objects having a temperature above absolute zero. The mid-infrared spectrum covers electromagnetic radiation with wavelengths in a range of approximately 2-25 µm. By measuring changes in the MIR spectrum, sensors are able to measure changes in a sample's chemistry or temperature, for example.

DETAILED DESCRIPTION

Figure 1A:
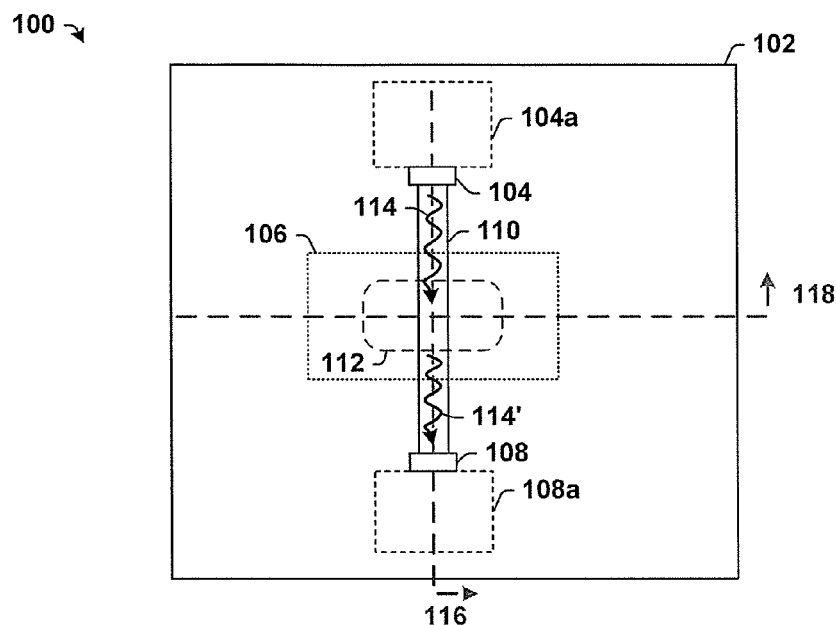
FIG. 1A is a block diagram of a top view of some embodiments of a disclosed infrared (IR) opto-electronic sensor.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details.

Infrared spectroscopy is performed using radiation in the infrared region of the electromagnetic spectrum (i.e., radiation having wavelengths of approximately 2-25 µm). Many modern days sensors use the infrared region of the electromagnetic spectrum to measure properties of fluid and/or gas samples. Such sensors generate IR radiation, which when brought into contact with the samples, reacts with the samples to cause a change (e.g., attenuation) in the IR radiation. The sensors then measure the changes in the IR radiation spectrum to determine properties of the samples.

The measurement of characteristic absorption of samples in the IR radiation spectrum, which represent a chemical fingerprint as particular substances, show stronger absorption at certain wavelengths being characteristic for the substance. This feature can be used by exposing the substance to broadband IR radiation and determining the absorption in the spectrum after the radiation has passed through or partly penetrated the sample.

In recent years, sensor research has experienced intensive growth as the number of areas of in which sensors are used has increased. As sensors are placed into more diverse applications the challenges for the sensor devices are becoming more complex. One such challenge is to form sensors that are compatible to and integrated within silicon-based technologies. By integrating sensors into silicon-based technologies, the sensors for instance can be easily fabricated onto a single integrated chip with other components such as processors, memory, etc.

The present disclosure relates to an opto-electronic sensor comprising a silicon waveguide implemented on a single integrated chip. In some embodiments, the IR sensor comprises a radiation source configured to generate radiation and a radiation detector configured to measure one or more properties of the radiation. A silicon waveguide (i.e., an optical waveguide made of silicon) extends along a length between the radiation source and the radiation detector. The silicon waveguide is configured to convey the radiation from the radiation source to the radiation detector at a single mode. The conveyed radiation forms an evanescent field that extends outward from the silicon waveguide to interact with a sample positioned in portions of the evanescent field. As the evanescent field interacts with the sample the radiation guided by the silicon waveguide is attenuated according to one or more characteristics of the sample (e.g., in particular, the radiation is absorbed in a wavelength region corresponding to the wavelength of the guided wave or waves). The radiation detector is configured to receive the attenuated MIR radiation and to determine the one or more characteristics of the sample from the attenuated MIR radiation.

FIG. 1A is a block diagram of a top view 100 of some embodiments of a disclosed infrared opto-electronic sensor (IR sensor).

The IR sensor comprises a radiation input conduit 104, an interaction volume 106, and a radiation output conduit 108. A semiconductor substrate 102 comprises a silicon waveguide 110 that extends along a length between the radiation input conduit 104 and the radiation output conduit 108. It will be appreciated that in various embodiments, the semiconductor substrate 102 may have varying features. For example, the silicon substrate may comprise microstructures (e.g., a regular pattern of holes forming so-called photonic crystals), layers of other materials (e.g., silicon nitride) between silicon waveguide 102 and an underlying silicon-substrate, and/or cavities located on a backside of the substrate extending under the silicon waveguide 102.

The radiation input conduit 104 is configured to couple infrared (IR) radiation into the silicon waveguide 110 (i.e., a waveguide made of silicon), located on the semiconductor substrate 102 (e.g., a silicon substrate), from a radiation source 104a configured to emit radiation 114. In some embodiments, the radiation 114 comprises mid-infrared (MIR) radiation (e.g., an electro-magnetic field having a wavelength in the mid-infrared region of the electromagnetic spectrum from approximately 2 μm to approximately 25 μm), while in other embodiments the radiation may comprise different wavelengths (e.g., near infrared radiation, having wavelength between 750 nm and 1 mm). In various embodiments, the radiation source 104a may comprise a radiation source integrated into the semiconductor substrate 102 (i.e., a radiation source 104a disposed within semiconductor substrate 102) or an external radiation source (e.g., a laser) located external to the semiconductor substrate 102 (i.e., a separate component in communication with the silicon waveguide 110).

The silicon waveguide 110 intersects the interaction volume 106, which contains a sample 112 (e.g., a liquid, gas, etc.) to be analyzed. The silicon waveguide 110 is configured to convey the radiation 114 from the radiation input conduit 104 to the radiation output conduit 108 with a low degree of attenuation. As the radiation 114 is conveyed through the interaction region, it interacts with the sample 112 which causes an attenuation which is distinct at characteristic wavelengths. As the radiation 114 interacts with the sample 112, spectrum of the radiation 114 changes, resulting in attenuated radiation 114' having a spectrum that defines one or more characteristics of the sample 112.

The radiation output conduit 108 is configured to couple infrared (IR) radiation from the silicon waveguide 110 to a radiation detector 108a. In some embodiments, the radiation detector 108a comprises a radiation detector integrated into the semiconductor substrate 102, while in other embodiments the radiation detector 108a comprises an external radiation detector. The radiation detector 108a is configured to receive the attenuated radiation 114' and to measure one or more characteristics of the attenuated radiation 114' therefrom. For example, in some embodiments the radiation detector 108a is configured to measure the intensity of the attenuated radiation 114'. By measuring the intensity of the attenuated radiation 114', the radiation detector 108a can determine one or more characteristics of the sample 112 due to attenuation at selected frequencies.

Figure 1B:
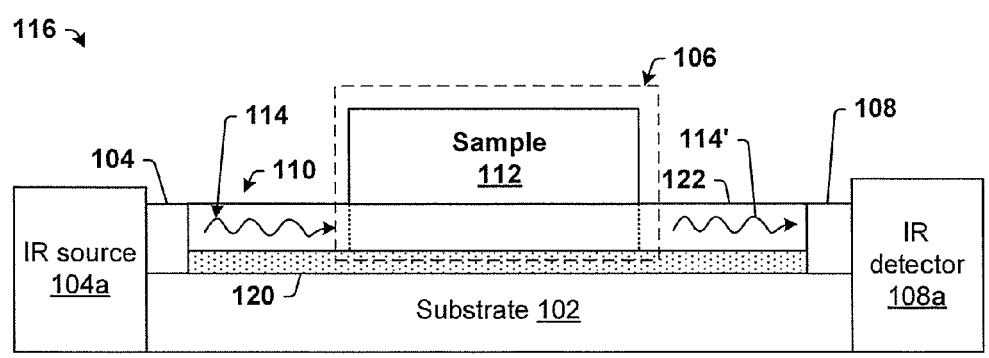
FIGS. 1B-1C illustrate cross-sectional views of the infrared (IR) opto-electronic sensor of FIG. 1A.

FIG. 1B illustrates a block diagram of a cross-sectional view 116 along a first direction of the IR sensor of FIG. 1A.

As shown in cross-sectional view 116, the IR sensor comprises a semiconductor substrate 102. In some embodiments, the semiconductor substrate 102 comprises a crystalline silicon substrate (e.g., having a <100> crystal orientation) optionally having an n-type or p-type dopant concentration. A buffer layer 120 is located above the semiconductor substrate 102. The silicon waveguide 110 is comprised within a silicon layer 122 located above the buffer layer 120. The buffer layer 120 is positioned to separate the semiconductor substrate 102 from the silicon waveguide 110. For example, in some embodiments, the buffer layer 120 is positioned below the silicon layer 122 that comprises the silicon waveguide 110 in an area that extends along a length of the silicon waveguide 110 from the radiation input conduit 104 to the radiation output conduit 108.

The buffer layer 120 comprises a material that has a different (e.g., larger) refractive index than the semiconductor substrate 102. For example, in some embodiments, the buffer layer 120 may comprise a silicon nitride (e.g., $SiN_3$) layer (n=1.98) or an amorphous carbon layer (n≈2.3) having a lower index of refraction than a silicon substrate (n=3.45079). The difference in the refractive indices of the buffer layer 120 and the semiconductor substrate 102 provides for optical isolation between the silicon waveguide 110 and the underlying semiconductor substrate 102. In some embodiments, the buffer layer 120 comprises a single layer, while in alternative embodiments the buffer layer 120 comprises a multiple layers of different materials (e.g., two different materials) which, by means of interference effects, achieve optical insulation at designated wavelengths. In some embodiments, in order to improve optical isolation between the silicon waveguide 110 and the semiconductor substrate 102, the semiconductor substrate 102 may comprise one or more backside cavities. The backside cavities comprise regions below the silicon waveguide 110 in which the silicon substrate 202 has been removed, as described in more detail below.

Optically insulating the silicon waveguide 110 from the semiconductor substrate 102 prevents the radiation 114 guided by the silicon waveguide from entering into the semiconductor substrate 102 and causing the IR sensor to malfunction (e.g., if the semiconductor substrate 102 comprises a silicon substrate, the radiation 114 would travel freely from the silicon waveguide 110 to the silicon substrate preventing the silicon waveguide 110 from operating properly).

Figure 1C:
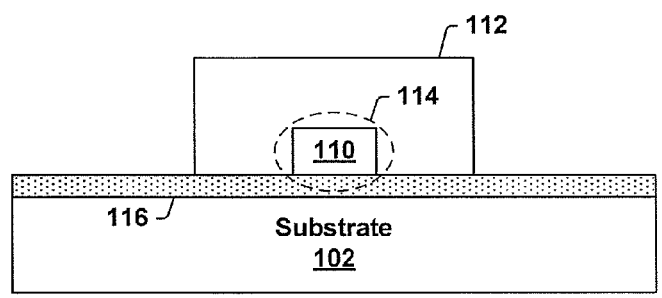

FIG. 1C illustrates a block diagram of a cross-sectional view 118 along a second direction of the IR sensor of FIG. 1A. Although cross-sectional view 118 illustrates the silicon waveguide 110 as a rib type waveguide located on top of the buffer layer 120, it will be appreciated that the silicon waveguide 110 is not limited to such a waveguide structure. For example, in some other embodiments the silicon waveguide 110 may comprise a photonic crystal waveguide disposed within a silicon layer. Furthermore, although illustrated as having a cross section that is substantially square, the disclosed silicon waveguide 110 is not limited to such a cross-sectional shape.

As shown in cross-sectional view 118, one or more surfaces of the silicon waveguide 110 are exposed to an ambient environment. By exposing one or more surfaces of the silicon waveguide 110 an ambient environment, the sample 112 is in direct contact with the silicon waveguide 110. While the radiation 114 is generally contained within the silicon waveguide 110, a small evanescent field of the radiation 114 extends outwards from the silicon waveguide 110 into an area around the silicon waveguide 110. The evanescent field interacts with the sample 112, which will absorb the radiation 114 with a specific spectral profile within the evanescent field so that the attenuated radiation 114' received at the radiation detector 108a has a spectrum that is indicative of one or more characteristics of the sample 112.

Figure 2:
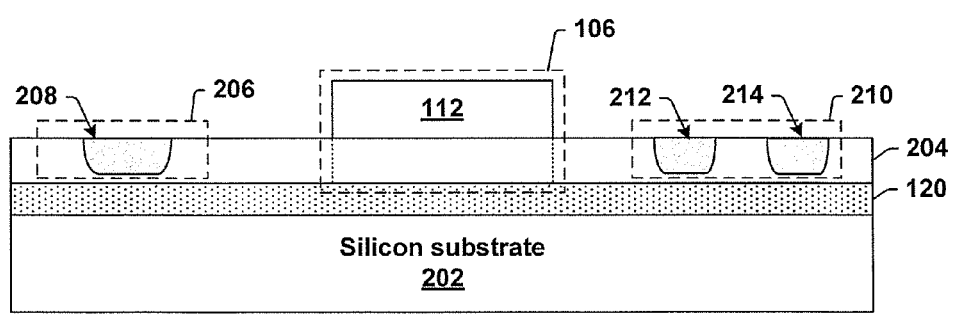
FIG. 2 is a cross-sectional view of some embodiments of an IR sensor having an emitter integrated into the waveguide.

FIG. 2 is a cross-sectional view 200 of some embodiments of a IR sensor having an infrared radiation (IR) source 206 and an IR detector 210 integrated into a silicon waveguide 204. The IR source 206 and the IR detector 210 are located along a plane that extends along the length of the silicon waveguide 204, thereby enabling the IR sensor to be easily manufactured on a single integrated chip.

In some embodiments, the IR source 206 comprises a resistive element. In various embodiments, the resistive element may comprise a polysilicon resistor, a thin film resistor, or some other similar resistive element. The resistive element is configured to receive a current from a current source (not shown). As the current flows through the resistive element, thermal energy is dissipated from the resistive element as a broadband infrared spectrum. In some embodiments, a filtering element is positioned between the resistive element and the silicon waveguide 204 to filter the broadband infrared spectrum in a manner that provides for a narrowband infrared radiation that is conveyed by the silicon waveguide 204. In some embodiments, the filtering element comprises a photonic crystal waveguide configured to filter the broadband radiation emitted from the resistive.

In one particular embodiment, the resistive element comprises a diffusion resistor having a doped region 208 with a first doping type located within a substrate having a second doping type. In some embodiments, the doped region 208 of the diffusion resistor comprises a p-type well located within an n-type silicon waveguide. In other embodiments, the doped region 208 of the diffusion resistor is integrated within the substrate at a location that is out of the plane of the silicon waveguide 204.

The IR radiation generated by the resistive element is guided by the silicon waveguide 204 from the IR source 206 to an IR detector 210 integrated within the silicon waveguide 204. In some embodiments, the IR detector 210 comprises a pin diode. The pin diode may comprise a horizontal pin diode having a first doped region 212 having a first doping type (e.g., p-type) and a second doped region 214 having a second doping type (e.g., n-type). Alternatively, the pin diode may comprise a vertical pin having a bottom p-layer formed by boron doping of the silicon waveguide 204, a top n-layer formed by antimony doping of the silicon waveguide 204, and an active intrinsic layer comprising germanium quantum dots and un-doped silicon.

Figure 3A:
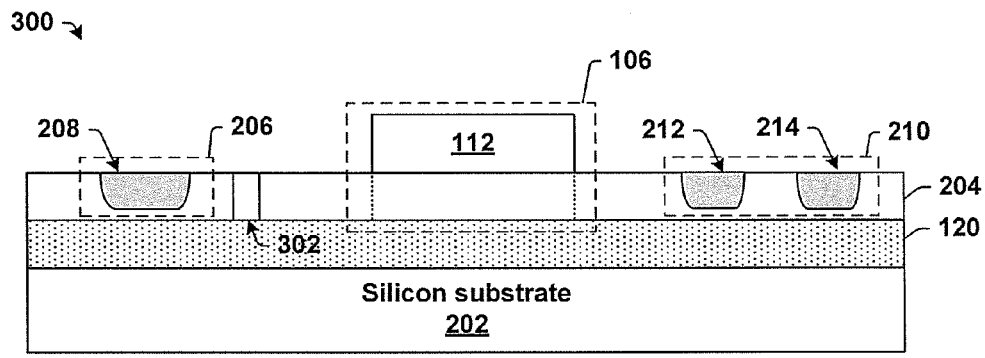
FIGS. 3A-3B illustrate cross-sectional views of some additional embodiments of an IR sensor having an emitter integrated into the waveguide.

FIG. 3A illustrates a cross-sectional view of some additional embodiments of an IR sensor having an IR source 206 and an IR detector 210 integrated into a silicon waveguide 204.

The silicon waveguide 204 comprises a coupling structure 302 positioned between the IR source 206 and the interaction volume 106. The coupling structure 302 comprises a material having a refractive index that is optimized to achieve efficient coupling of infrared radiation from the IR source 206 into the silicon waveguide 204. The chosen refractive index allows for radiation emitted from the IR source 206 to be efficiently transmitted to the interaction volume 106, while providing for thermal insulation that prevents heat conduction to the interaction volume 106. In some embodiments, the coupling structure 302 may comprise an area of air or vacuum.

Although the coupling structure 302 is illustrated with an IR sensor having an IR source 206 integrated into a silicon waveguide 204, it will be appreciated that in alternative embodiments the coupling structure 302 may be implemented in an IR sensor having an IR source placed in close proximity to a silicon waveguide 204 (e.g., out of the plane of the waveguide).

Figure 3B:
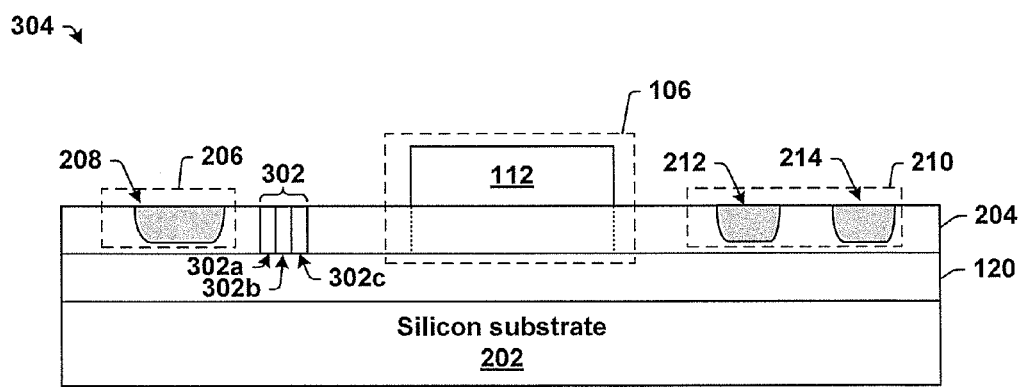

In some embodiments, the coupling structure 302 comprises a plurality of separate layers comprising two or more different materials. For example, FIG. 3B illustrates a cross-sectional view 304 of an IR sensor having a coupling structure 302 comprising a plurality of separate layers 302a, 302b, and 302c extending from a top surface of the silicon waveguide 204 to the underlying buffer layer 120. In such embodiments, the separate layers 302a, 302b, and 302c of the coupling structure 302 generate interference in the radiation generated by the IR source 206, resulting in optical impedance matching between the IR source 206 and the silicon waveguide 204.

Figure 4:
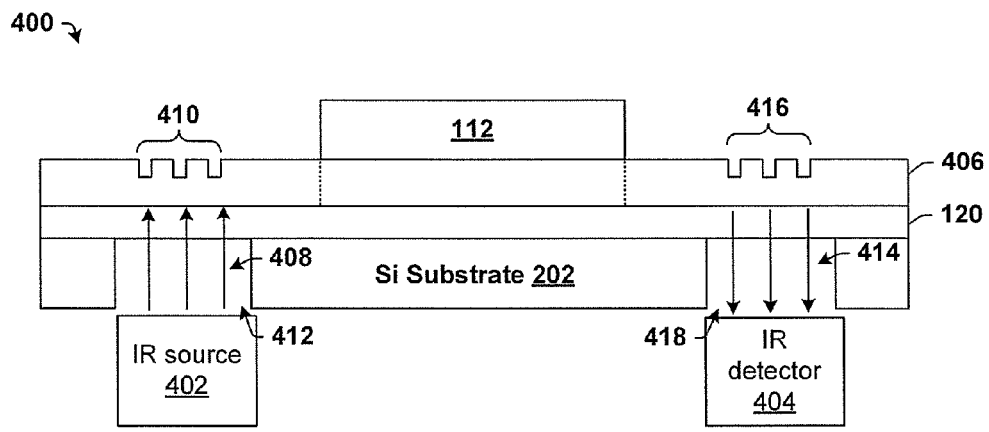
FIG. 4 illustrates a cross-sectional view of some additional embodiments of an IR sensor having an emitter out of the plane of a waveguide.

FIG. 4 illustrates a cross-sectional view 400 of some additional embodiments of an IR sensor having an integrated IR source 402 and an integrated IR detector 404 located out of the plane of a silicon waveguide 406.

The IR source 402 is configured to generate an electromagnetic field 408 with a significant infrared spectrum (e.g., an electromagnetic field having a wavelength in the mid-infrared region from approximately 2 µm to approximately 25 µm or in the near infrared region from between approximately 750 nm and 1 mm). An IR spectrum of the electromagnetic field 408 is coupled to the silicon waveguide 406 by a first coupling element 410 located at a first end of the silicon waveguide 406. The first coupling element 410 is configured to convert the electromagnetic field 408 to IR radiation having a guided mode that is guided by the silicon waveguide 406. In some embodiments, the first coupling element 410 comprises a grating coupler having a plurality of periodically arranged cavities in a top surface of the silicon waveguide 406. In other embodiments, the first coupling element 410 may comprise a prism configured to couple IR radiation into the silicon waveguide 406, for example.

In some embodiments, the IR source 402 is located along a backside of the silicon substrate 202 and is in communication with the silicon waveguide 406 by way of a first cavity 412 in the backside of the silicon substrate 202. The first cavity 412 vertically extends from a backside of the silicon substrate 202 to a buffer layer 120 and improves transmission of the electromagnetic field 408 to the silicon waveguide 406.

In order to measure the attenuated IR radiation, a second coupling element 416 is located at a second end of the silicon waveguide 406, opposite the first end. The second coupling element 416 is configured to couple the IR radiation 414 out of the silicon waveguide 406 towards the IR detector 404. In some embodiments, the IR detector 404 is located along a backside of the silicon substrate 202 and is in communication with the silicon waveguide 406 by way of a second cavity 418 in the backside of the silicon substrate 202. In some embodiments, the IR detector 404 may be located at an angle with respect to the second coupling element 416, so that angular coupling characteristics of the second coupling element 416 to perform spectral separation of the IR radiation 414.

Figure 5:
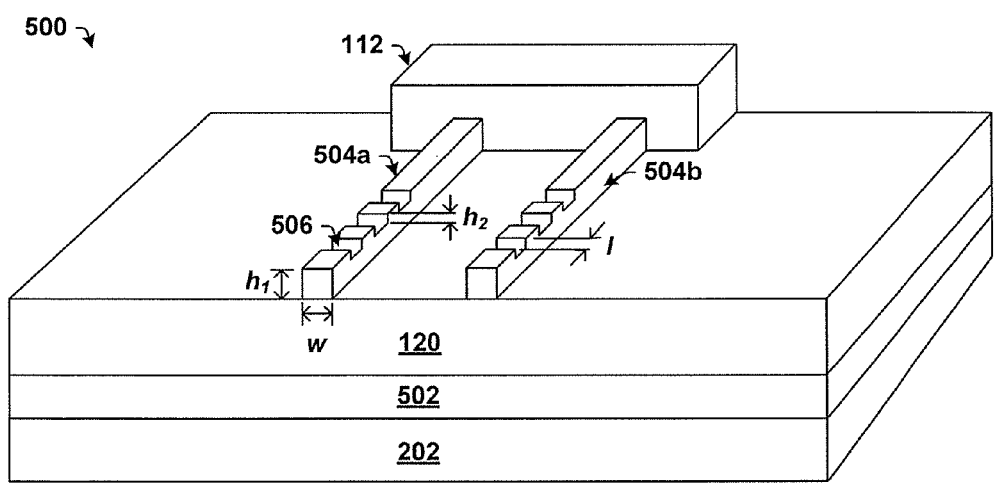
FIG. 5 is a three-dimensional view of some embodiments of an IR sensor having one or more silicon rib waveguides.

FIG. 5 is a three-dimensional view 500 of some embodiments of an IR sensor having one or more silicon rib waveguides 504.

The one or more silicon rib waveguides 504 extend over a top surface of a buffer layer 120 (e.g., comprising one or more separate layers), which may be connected to a silicon substrate 202 by way of an adhesion layer 502 (e.g., $SiO_2$) configured to improve adhesion between the buffer layer and the silicon substrate. Respective silicon rib waveguides 504 comprise a silicon fin extending vertically outward from a top surface of the buffer layer 120. In some embodiments, the silicon rib waveguide 504 is corrugated to have a plurality of ridges 506 located along a top surface of the waveguide. The corrugated section of the waveguide comprises a grating coupler that enables IR radiation to be coupled into or out of the silicon rib waveguide 504.

In some embodiments, the IR sensor comprises a plurality of silicon rib waveguides 504a and 504b disposed in parallel to one another and separated by a distance that allows for the waveguides to concurrently interact with a sample 112. By increasing the number of silicon rib waveguides 504 interacting with a sample 112, the sensitivity of the IR sensor is increased. For example, a IR sensor comprising two silicon rib waveguides 504a and 504b that interact with a sample 112 will have a greater sensitivity than an IR sensor having a single silicon rib waveguide 504a or 504b that interacts with the sample 112.

It will be appreciated that the dimensions of a disclosed waveguide control operation of the waveguide. For example, by properly tuning a width w or height $h_1$ of a silicon rib waveguide 504, a desired spectral range of the waveguide operation can be obtained. For example, the height $h_1$ of a silicon rib waveguide 504 can be adjusted to change the IR sensor's sensitivity (e.g., a smaller height $h_1$ provides for a stronger interaction of the evanescent field and the sample 112). Varying the dimensions of a disclosed silicon waveguide can also vary the wavelength of radiation transmitted by the waveguide. For example, to perform analysis of a sample at a wavelength of MIR radiation around 5 μm, a silicon rib waveguide can be formed having a 2 μm width and a 600 nm height for an operation wavelength.

In some embodiments, the dimensions of the disclosed IR sensor are chosen so that the one or more silicon rib waveguides 504 comprise a single-mode Si waveguide (WG) that support one transverse electric (TE) mode and one transverse magnetic (TM) mode (e.g., fundamental modes $TE_{00}$ and $TM_{00}$). The single-mode waveguide avoids losses due to imperfections on the silicon waveguide walls causing redistribution of the carried energy among the different modes.

The inventors have appreciated that leakage from a disclosed silicon waveguide to an underlying silicon substrate may intrinsically attenuate the IR radiation in the disclosed silicon waveguide, leading to leaky waves. To prevent such leakage and achieve a high degree of isolation between a disclosed silicon waveguide and an underlying silicon substrate, a relatively thick buffer layer can be used. However, processing difficulties may arise in forming buffer layers having a large thickness (e.g., greater than approximately 1 μm).

Figure 6:
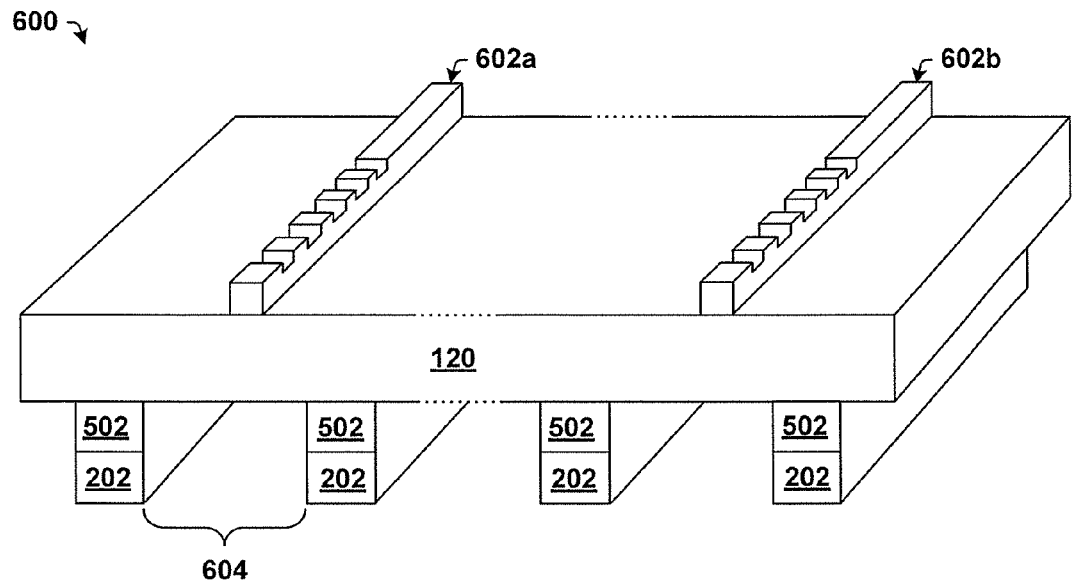
FIG. 6 is a three-dimensional view of some alternative embodiments of an IR sensor having one or more silicon rib waveguides located above one or more cavities in the backside of a silicon substrate.

Therefore, in some embodiments, optical isolation between IR radiation in a disclosed silicon waveguide and an underlying silicon substrate can be provided by removing the silicon substrate below the silicon waveguide. For example, FIG. 6 is a three-dimensional view 600 of some alternative embodiments of an IR sensor having one or more silicon rib waveguides 602.

The silicon rib waveguides 602 are positioned on a top surface of a substrate comprising a silicon substrate 202 and an adhesion layer 502. A backside of the substrate, opposite the top surface, comprises one or more backside cavities 604 positioned beneath a silicon rib waveguide 602. The one or more backside cavities vertically extend from a backside of the substrate to a buffer layer 120 underlying the silicon rib waveguide 602. Having one or more backside cavities 604 below the silicon rib waveguide 602 causes the silicon rib waveguides to be supported by a thin membrane comprising the buffer layer 120. In some embodiments, the thin membrane comprises a buffer layer 120 having a single material featuring a refractive index lower than that of the waveguide (e.g., silicon). For example, in some embodiments, the thin membrane comprises low refractive index $Si_3N_4$ membrane.

In some embodiments, the one or more backside cavities 606 laterally extend along the backside of the silicon substrate 202 in a direction that is parallel to the silicon rib waveguide 602. In some embodiments a single backside cavity extends along a length of the silicon rib waveguide 602, while in other embodiments a series of backside cavities extend along a length of the silicon rib waveguide 602. Such an orientation of the backside cavities 604 effectively removes the silicon substrate 202 from below the silicon rib waveguide 602, thereby providing for efficient propagation of the IR radiation down the waveguide by preventing attenuation of IR radiation by the silicon substrate 202.

Figure 7A:
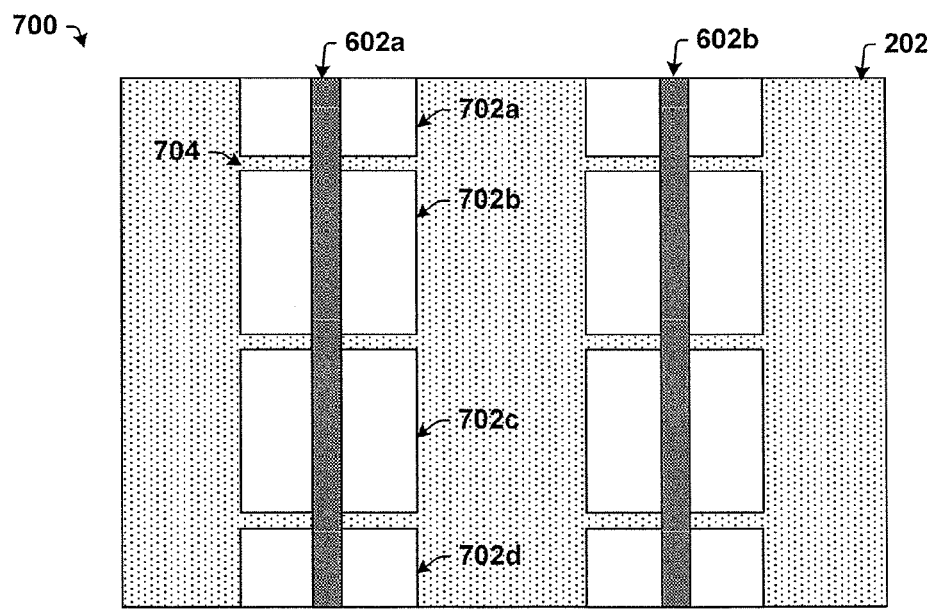
FIGS. 7A-7B illustrate top views of some embodiments a backside of the silicon substrate of FIG. 6.
Figure 7B:
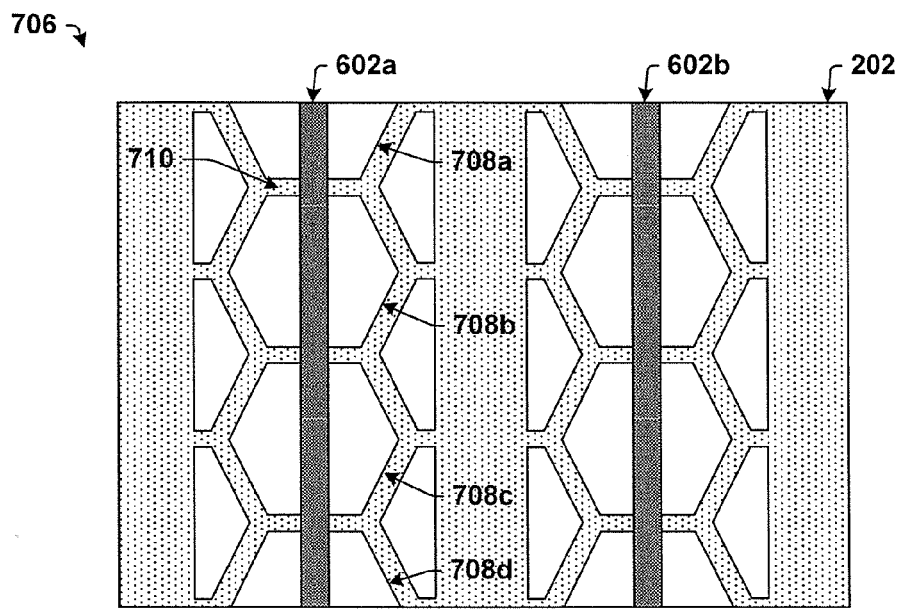

FIGS. 7A-7B illustrate some embodiments of top views, 700 and 706, of the backside of the silicon substrate. As shown in the top view 700 of FIG. 7A, backside cavities within the substrate comprise substantially square cavities 702 in the backside of the silicon substrate 202. In some embodiments, the square cavities 702 are oriented to provide for a series of square cavities 702a-702d that extend along a length of the silicon rib waveguide 602a. In such an embodiment, un-etched areas between adjacent square cavities 702 form silicon beams 704 that provide structural support for the thin membrane below the silicon rib waveguide 602. In various embodiments, the silicon beams 704 may have a thickness that is equal to a thickness of the silicon substrate 202 or a thickness that is smaller than the thickness of the silicon substrate 202 (i.e., a thickness that is smaller than that of the cavity 702).

In other embodiments, the backside cavities may comprise hexagonal cavities 708 (having a hexagonal shape), as shown in the top view 706 of FIG. 7B. In some embodiments, the hexagonal cavities 708 are oriented to provide for a series of hexagonal cavities 708a-708d that extend along a length of the silicon rib waveguide 602a. In such an embodiment, un-etched areas between adjacent hexagonal cavities 708 form silicon beams 710 that provide structural support for the thin membrane below the silicon rib waveguide 602a. In various embodiments, the silicon beams 710 may have a thickness that is equal to a thickness of the silicon substrate 202 or a thickness that is smaller than the thickness of the silicon substrate 202. The hexagonal cavities 708 provide for greater structural support of the membrane supporting the silicon rib waveguide 602a than a single backside cavity extending along a length of the waveguide or a series of square cavities extending along a length of the waveguide (e.g., as shown in FIG. 7A).

In yet other embodiments, a region of the semiconductor substrate located below the disclosed silicon waveguide may comprise a plurality of backside cavities comprising a periodic perforation of micro-cavities. For example, the region of the semiconductor substrate located below the disclosed silicon waveguide may be perforated by round holes that provide for an array of micro-cavities positioned in a periodic along the backside of the semiconductor substrate. The micro-cavities have a diameter that is smaller than a width of the silicon waveguide so that more than one micro-cavity may be positioned along a width of the silicon waveguide. The micro-cavities have a depth that extends from a back side of the semiconductor substrate to the buffer layer so as to remove the silicon substrate from below the silicon waveguide. By removing the silicon substrate from below the silicon waveguide, the micro-cavities reduce leakage of radiation from the silicon waveguide to the semiconductor substrate.

Figure 8:
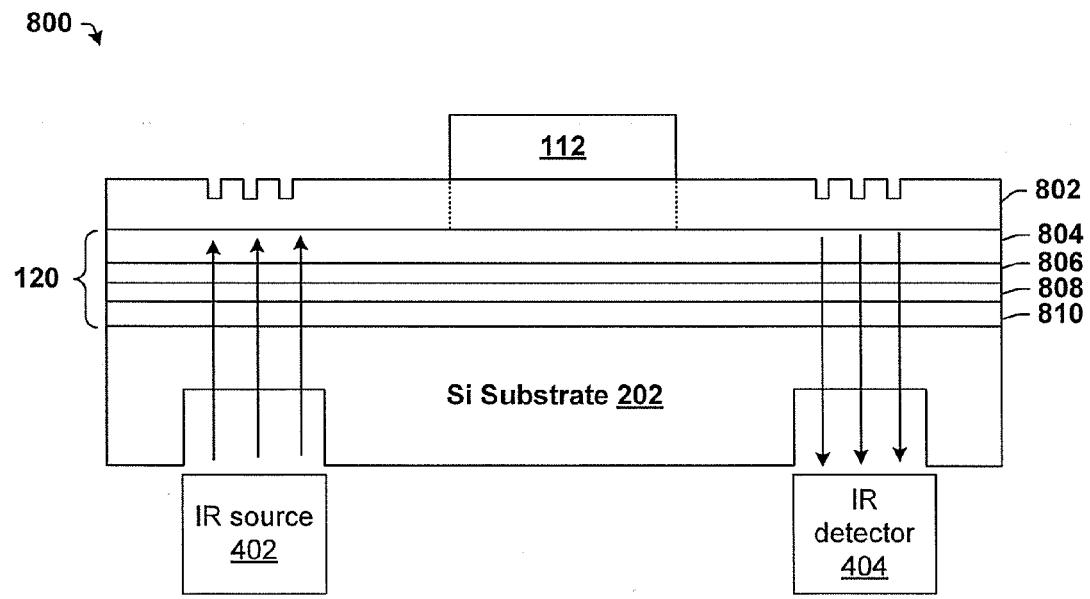
FIG. 8 illustrates a cross-sectional view of some alternative embodiments of an IR sensor having a plurality of dielectric layers configured to provide optical isolation between a silicon waveguide and underlying substrate.

FIG. 8 illustrates a cross-sectional view 800 of some alternative embodiments of an IR sensor having a buffer layer 120 comprising a plurality of dielectric layers 804-810 positioned between a silicon waveguide 802 and an underlying silicon substrate 202. The plurality of dielectric layers 804-810 are configured to provide a high degree of optical isolation between the silicon waveguide 802 and the silicon substrate 202

In some embodiments, the plurality of dielectric layers 804-810 are disposed on top of one another so that the plurality of dielectric layers 804-810 form a plurality of interfaces at which different refractive indices meet. In some embodiments, the plurality of dielectric layers 804-810 are chosen to have thicknesses and refractive indices that form a Bragg mirror (i.e., a dielectric mirror) that prevents IR radiation from the silicon waveguide 802 from reaching the silicon substrate 202.

It will be appreciated that the material and/or thickness of respective dielectric layers 804-810 may vary depending on a degree of reflectivity and/or a wavelength of radiation to be reflected. In some embodiments, the plurality of dielectric layers 804-810 may be chosen to reflect a narrowband of radiation corresponding to the radiation that is present in the silicon waveguide 802. In some embodiments, the plurality of dielectric layers 804-810 may comprise one or more of magnesium fluoride or silicon dioxide, for example.

Figure 9A:
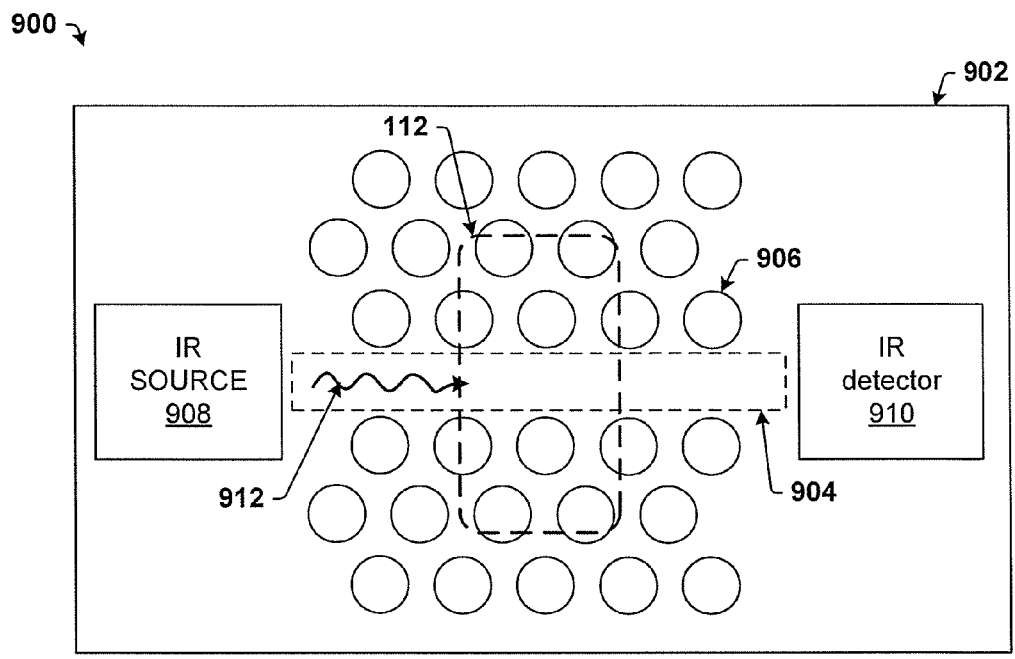
FIG. 9A illustrates a top view of some embodiments of an IR sensor having a photonic crystal waveguide.

FIG. 9A illustrates a top view 900 of some embodiments of an IR sensor having one or more photonic crystal waveguides.

The photonic crystal waveguides comprise a plurality of cavities 906 in a silicon layer 902 on a semiconductor substrate. The cavities 906 are laterally disposed along opposing sides of a photonic crystal waveguide region 904 along a length of the waveguide extending between an IR source 908 and an IR detector 910. In various embodiments, the cavities 906 may comprise circular holes in the silicon layer 902, while in other embodiment the cavities 906 may comprise other shapes in the silicon layer 902.

The cavities 906 are arranged to allow for wavelengths outside of the IR spectrum to freely propagate within the silicon layer 902, but to prevent wavelengths within the desired part of the IR spectrum from propagating outside of the photonic crystal waveguide region 904. For example, if the IR source 908 outputs a broadband signal, the cavities 906 will block a narrow band of IR radiation so that the narrow band will not leak away to the left and right of the photonic crystal waveguide region 904. Instead the narrow band of radiation will be guided along the photonic crystal waveguide region 904 as IR radiation 912. In some embodiments, the cavities 906 are arranged according to a periodic pattern having an equal spacing from one another.

In some embodiments, the cavities 906 may be configured to filter unwanted wavelengths from the photonic crystal waveguide region 904 so that a subset of the infrared spectrum is guided by the waveguide. In other embodiments, the photonic crystal waveguide region 904 may further comprise a coupling element (e.g., a grating coupler) configured to couple desired wavelengths into the waveguide. The coupling element can be used to improve filtering performed by the cavities 906.

Figure 9B:
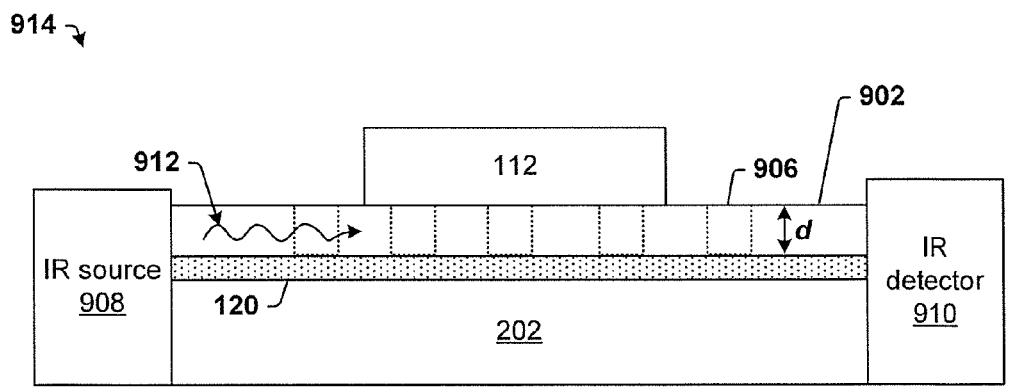
FIG. 9B illustrates a cross-sectional view of some embodiments of an IR sensor having a photonic crystal waveguide.

FIG. 9B illustrates a cross-sectional view 914 of some embodiments of an IR sensor having one or more photonic crystal waveguides.

As illustrated in cross-sectional view 914 the cavities 906 extend from a top surface of the silicon layer 902 to a depth d that defines a height of the photonic crystal waveguide. In some embodiments the cavities 906 extend from a top surface of the silicon layer 902 to an underlying buffer layer 120. The sample 112 is located on top of the silicon layer 902 so that the sample is in contact with a top surface of the photonic crystal waveguide. Additionally, the sample 112 may fill one or more of the cavities 906 to contact the waveguide along one or more of its sides. In some embodiments, the silicon substrate 202 may further comprise one or more backside cavities as described above.

Figure 10:
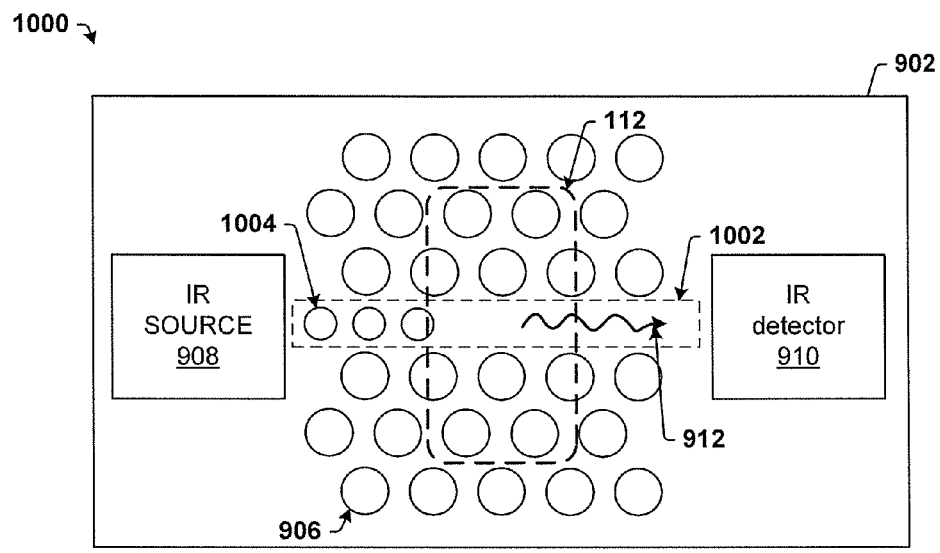
FIG. 10 is a top view of some alternative embodiments of an IR sensor having a photonic crystal waveguide.

FIG. 10 is a top view 1000 of some alternative embodiments of an IR sensor having a photonic crystal waveguide. The photonic crystal waveguide comprises one or more waveguide cavities 1004 within a waveguide region 1002 disposed between cavities 906 along a length of the waveguide extending between an IR source 908 and an IR detector 910. The waveguide cavities 1004 can be selected to have a dimension that operates to change/tune one or more guiding characteristics (e.g., propagation modes) of IR radiation 912 generated by the IR source 908. In some embodiments, the waveguide cavities 1004 can further be configured to operate as a coupling element that aids in coupling IR radiation into the waveguide region 1002.

In some embodiments the waveguide cavities 1004 extend from a top surface of the silicon layer 902 to a depth that is less than that of the surrounding cavities 906. In other embodiments, the waveguide cavities 1004 may alternatively or additionally have a smaller radius than the surrounding cavities 906. In some embodiments, cavities 906 are disposed within the silicon layer 902 with a first periodic spacing, while waveguide cavities 1004 are disposed within the silicon layer 902 with a second periodic spacing, greater than the first periodic spacing.

Figure 11:
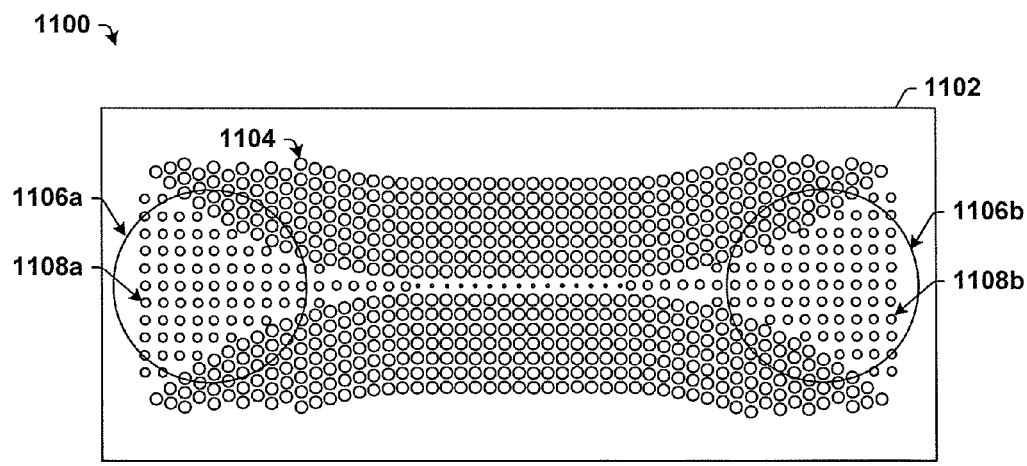
FIG. 11 illustrates a top view of a more detailed embodiment of an IR sensor having a photonic crystal waveguide.

FIG. 11 illustrates a top view 1100 of a more detailed embodiment of an IR sensor having a photonic crystal waveguide. The photonic crystal waveguide comprises a plurality of cavities 1104 within a silicon layer 1102 that define a waveguide region that is configured to convey IR radiation. A first coupler region 1106a is located at a first end of the waveguide region and a second coupler region 1106b is located at a second end of the waveguide region. The first coupler region 1106a comprises a plurality of waveguide cavities 1108a that are collectively configured to couple IR radiation into the waveguide region. The waveguide cavities 1108a are disposed in a tapered layout that has a narrower width towards a center of the waveguide region. The tapered layout facilitates coupling of obliquely or normally incident IR radiation and concentrate collected radiation that is conveyed through the waveguide region. The second coupler region 1106b comprises a plurality of waveguide cavities 1108b that are collectively configured to provide IR radiation out of the waveguide region. The waveguide cavities 1108ba are disposed in a tapered layout that mirrors the first coupler region (i.e., has a narrower width towards the center of the waveguide region).

Figure 12:
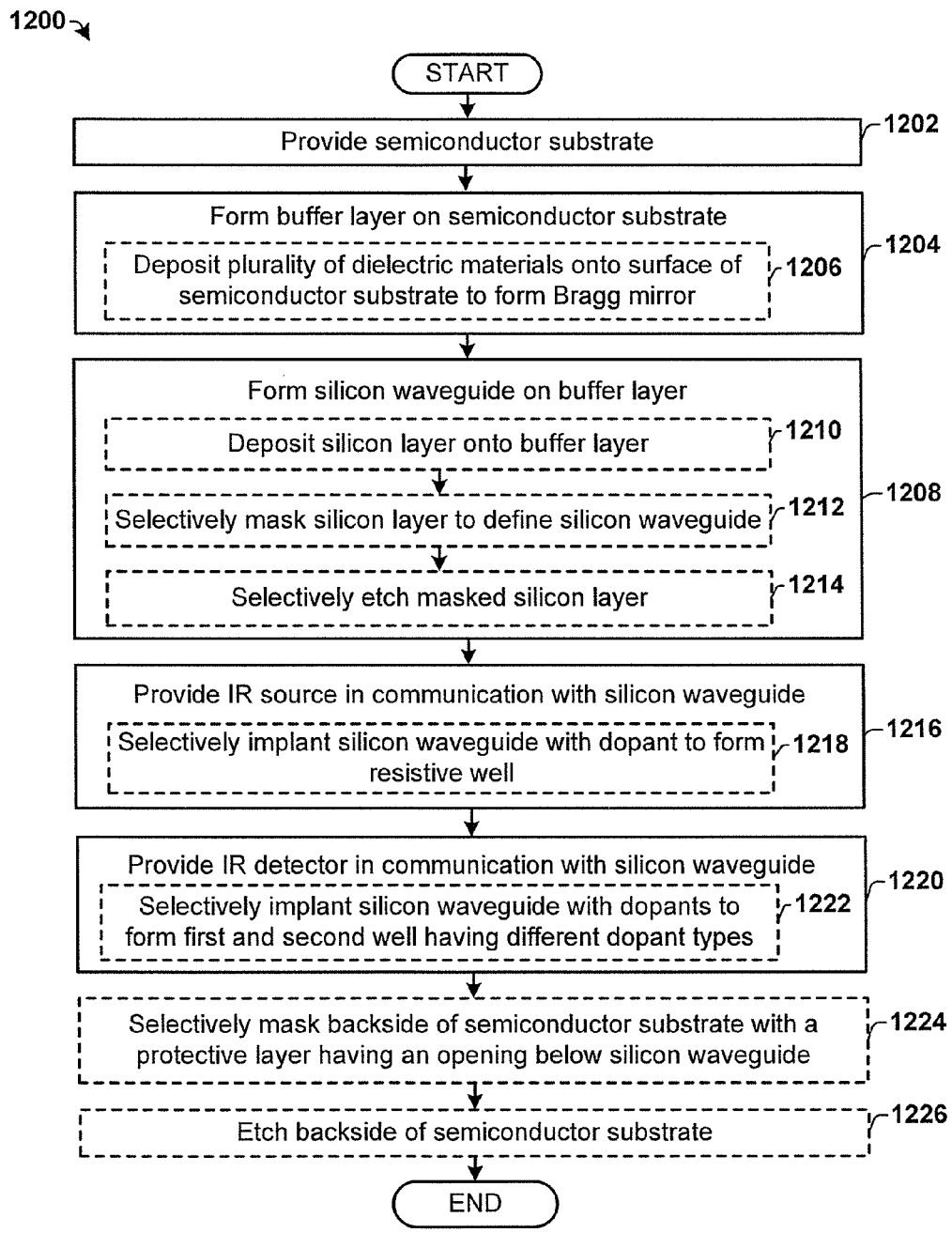
FIG. 12 is a flow diagram of an exemplary method of forming an IR sensor having a silicon waveguide.

FIG. 12 is a flow diagram of an exemplary method 1200 of forming an IR sensor having a silicon waveguide.

It will be appreciated that while method 1200 is illustrated and described below as a series of acts or events, the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the disclosure herein. Also, one or more of the acts depicted herein may be carried out in one or more separate acts and/or phases.

At 1202, a semiconductor substrate is provided. In some embodiments, the semiconductor substrate comprises a silicon substrate (e.g., a single-crystal silicon with a <100> orientation). In various embodiments the silicon substrate may be doped with an n-type or p-type dopant concentration or may not be doped. In other embodiments, the semiconductor substrate may comprise a silicon substrate with an epitaxial layer.

At 1204, a buffer layer is formed on the semiconductor substrate. The buffer layer may be formed on the semiconductor substrate using a physical vapor deposition (e.g., evaporation, sputtering, etc.). In some embodiments, the buffer layer may comprise silicon nitride or an amorphous carbon layer. In some embodiments, forming the buffer layer comprises consecutively depositing a plurality of dielectric layers (at 1206) on the surface of the substrate in a manner that forms a Bragg mirror having a high reflectivity to IR radiation.

At 1208, a silicon waveguide is formed above the buffer layer. In various embodiments, the silicon waveguide may comprise a silicon rib waveguide or a photonic crystal waveguide.

In some embodiments, the silicon waveguide is formed by forming a silicon layer on the buffer layer at 1210. The silicon layer may be formed by depositing a silicon layer using a physical vapor deposition. At 1212, the silicon layer is selectively masked. In some embodiments, the silicon layer is selectively masked by forming a first masking layer that defines one or more silicon waveguides. In some embodiment, the first masking layer comprises a patterned photoresist layer formed on the surface of the silicon layer by way of a spin coating process. The spin coated photoresist is then patterned by selective exposure to a light source (e.g., UV light) and subsequently developed. At 1214, the silicon layer is selectively etched to form the waveguide according to the first masking layer.

At 1216, an IR source is provided in communication with a first end of the silicon waveguide. The IR source is configured to emit radiation comprising mid-infrared (MIR) radiation or near infrared radiation, in some embodiments. In some embodiments, the IR source comprises a diffusion resistor, formed by selectively implanting the silicon layer with a dopant (at 1218). The dopant may comprise a p-type dopant (e.g., boron, gallium, etc.) or an n-type dopant (e.g., phosphorus, arsenic, etc.). In some embodiments, an n-type dopant is implanted into a p-type substrate at a dose having a range of approximately $10^{12}$-$10^{17}$ cm$^{-3}$.

At 1220, an IR detector is provided in communication with a second end of the silicon waveguide. In some embodiments, the IR detector comprises a pin diode, formed by selectively implanting the silicon layer with a first and second well having different dopant types (at 1222).

At 1224, the backside of the substrate is selectively masked with a protective layer, in some embodiments. The protective layer forms an opening that is located below the silicon waveguide. In various embodiments, the protective layer may comprise a hardmask (e.g., SiN) that corresponds to a selected etching process of 1226.

At 1226, the backside of the substrate is selectively etched to remove the semiconductor substrate from below the silicon waveguide, in some embodiments. The semiconductor substrate can be etched to a depth that extends from the backside of the semiconductor substrate to the buffer layer. In some embodiments, the backside of the semiconductor substrate is etched using a deep reactive ion etch (e.g., a Bosch etch process). In other embodiments, the substrate is subjected to an electrochemically controlled etching (ECE) process, in which the substrate is immersed in an etchant (e.g., a KOH bath).

It will be appreciated that equivalent alterations and/or modifications may occur to those skilled in the art based upon a reading and/or understanding of the specification and annexed drawings. The disclosure herein includes all such modifications and alterations and is generally not intended to be limited thereby. For example, although the figures provided herein, are illustrated and described to have a particular doping type, it will be appreciated that alternative doping types may be utilized as will be appreciated by one of ordinary skill in the art.

In addition, while a particular feature or aspect may have been disclosed with respect to only one of several implementations, such feature or aspect may be combined with one or more other features and/or aspects of other implementations as may be desired. Furthermore, to the extent that the terms "includes", "having", "has", "with", and/or variants thereof are used herein, such terms are intended to be inclusive in meaning—like "comprising." Also, "exemplary" is merely meant to mean an example, rather than the best. It is also to be appreciated that features, layers and/or elements depicted herein are illustrated with particular dimensions and/or orientations relative to one another for purposes of simplicity and ease of understanding, and that the actual dimensions.

What is claimed is:

1. An infrared opto-electronic (IR) sensor, comprising:
a semiconductor substrate comprising a silicon waveguide consisting of silicon and continuously extending between a radiation input conduit configured to couple radiation into the silicon waveguide and a radiation output conduit configured to couple radiation from the silicon waveguide;
a buffer layer having a planar upper surface that continuously contacts a lower surface of the silicon waveguide between the radiation input conduit and the radiation output conduit, wherein the silicon waveguide is configured to convey the radiation from the radiation input conduit to the radiation output conduit at a single mode in a manner that results in an evanescent field that extends outward from the silicon waveguide to interact with a sample; and
a coupling element configured to couple radiation from a radiation source into the silicon waveguide, wherein the coupling element comprises a plurality of separate layers comprising different materials vertically extending from an upper surface of the silicon waveguide to the buffer layer and stacked in a direction horizontally extending along a length of the silicon waveguide.

2. The IR sensor of claim 1, further comprising:
a radiation source configured to generate the radiation that is coupled into the silicon waveguide at the radiation input conduit; and
a radiation detector configured to measure one or more characteristics of the radiation is coupled from the silicon waveguide at the radiation output conduit.

3. The IR sensor of claim 1, wherein the buffer layer is positioned between the semiconductor substrate and the silicon waveguide, wherein the buffer layer optically isolates the radiation from the semiconductor substrate.

4. The IR sensor of claim 3, wherein the buffer layer comprises an amorphous carbon layer.

5. The IR sensor of claim 3, further comprising:
one or more backside cavities positioned vertically below the silicon waveguide and vertically extending from a backside of the semiconductor substrate to the buffer layer.

6. The IR sensor of claim 3, wherein the silicon waveguide comprises a rib waveguide comprising a silicon fin located above the buffer layer.

7. An infrared opto-electronic (IR) sensor, comprising:
an infrared radiation (IR) source configured to generate IR radiation having a wavelength in an infrared region of the electromagnetic spectrum;
an infrared radiation (IR) detector configured to measure one or more properties of the IR radiation;
a silicon substrate;
a buffer layer located above the silicon substrate; and
a layer of silicon material arranged over the buffer layer and comprising the IR source, the IR detector, and a silicon waveguide consisting of silicon, wherein the IR source and the IR detector are arranged within the layer of silicon material at locations laterally offset from the silicon waveguide.

8. The IR sensor of claim 7, further comprising:
one or more backside cavities positioned vertically below the silicon waveguide and vertically extending from a backside of the silicon substrate to the buffer layer.

9. The IR sensor of claim 7, wherein the silicon waveguide comprises a rib waveguide comprising a silicon fin located above the buffer layer.

10. The IR sensor of claim 1,
wherein the radiation detector is located along a backside of the semiconductor substrate that faces away from the silicon waveguide, and
wherein the radiation detector is in communication with the silicon waveguide by way of a first cavity in the backside of the semiconductor substrate which extends from a backside of the semiconductor substrate to the buffer layer.

11. The IR sensor of claim 3, wherein the buffer layer is connected to the semiconductor substrate by way of an adhesion layer disposed between the buffer layer and the semiconductor substrate.

12. The IR sensor of claim 3, wherein the buffer layer comprises a plurality of dielectric layers disposed on top of one another so as to form a plurality of interfaces at which different refractive indices meet.

13. The IR sensor of claim 7,
wherein the IR detector comprises an IR path that extends from the layer of silicon to a backside of the silicon substrate that faces away from the silicon waveguide, and
wherein the IR detector is in communication with the silicon waveguide by way of a first cavity in the backside of the silicon substrate which extends from a backside of the silicon substrate to the buffer layer.

14. The IR sensor of claim 7, wherein the buffer layer comprises a plurality of dielectric layers disposed on top of one another so as to form a plurality of interfaces at which different refractive indices meet.

15. The IR sensor of claim 1, wherein the coupling element is configured to provide thermal insulation between the radiation source and the silicon waveguide without significantly attenuating the radiation in an infrared region of the electromagnetic spectrum.

16. The IR sensor of claim 7, further comprising:
a coupling element comprising one or more layers having a same height as the silicon waveguide and laterally arranged between the IR source and the silicon waveguide.

\* \* \* \* \*